United States Patent [19]

Aoyagi

[11] Patent Number: 4,940,541
[45] Date of Patent: Jul. 10, 1990

[54] BLOOD CLEANING HOLLOW FIBER MEMBRANE, METHOD FOR CLEANING BLOOD, AND APPARATUS THEREFOR

[75] Inventor: Juuro Aoyagi, Tokyo, Japan

[73] Assignee: Tokyo Bi-Tech Laboratories, Inc., Tokyo, Japan

[21] Appl. No.: 265,822

[22] Filed: Nov. 1, 1988

[30] Foreign Application Priority Data

| Feb. 11, 1987 | [JP] | Japan | 62-275749 |
| Apr. 11, 1987 | [JP] | Japan | 62-277486 |
| Apr. 11, 1987 | [JP] | Japan | 62-277487 |

[51] Int. Cl.$^5$ .............. B01D 63/02; B01D 63/04; B01D 65/02; B01D 69/08
[52] U.S. Cl. .............. 210/321.8; 210/335; 210/500.23; 422/22; 427/2; 427/36; 427/230; 427/400
[58] Field of Search .............. 210/253, 321.78–321.81, 210/321.87–321.9, 323.1, 332, 340, 500.23, 500.27–500.43, 503–506, 508, 638, 644–646, 649, 650, 653, 654, 791, 335; 424/101; 427/36, 400, 2, 230; 422/22

[56] References Cited

U.S. PATENT DOCUMENTS

| 3,727,612 | 4/1973 | Sayers et al. | 210/321.8 |
| 4,143,218 | 3/1979 | Adams et al. | 210/500.41 |
| 4,402,940 | 9/1983 | Nose et al. | 424/101 |
| 4,637,880 | 1/1987 | Halbert | 210/638 |
| 4,708,800 | 11/1987 | Ichikawa et al. | 210/500.23 |
| 4,717,479 | 1/1988 | Itoh et al. | 210/506 |
| 4,767,538 | 8/1988 | Jakubowski et al. | 210/636 |
| 4,780,205 | 10/1988 | Murakami et al. | 210/500.23 |

FOREIGN PATENT DOCUMENTS

| 0186758 | 7/1986 | European Pat. Off. . |
| 0222365 | 5/1987 | European Pat. Off. . |
| 0272841 | 6/1988 | European Pat. Off. . |
| 0302650 | 2/1990 | European Pat. Off. . |
| 56-52123 | 12/1981 | Japan . |
| 57-20970 | 5/1982 | Japan . |
| 61-90705 | 5/1986 | Japan . |
| 62-179540 | 8/1987 | Japan . |
| 1338810 | 11/1973 | United Kingdom . |

*Primary Examiner*—W. Gary Jones
*Attorney, Agent, or Firm*—Mathews, Woodbridge & Collins

[57] ABSTRACT

The present invention discloses a blood cleaning hollow fiber membrane characterized by comprising a hydrophobic porous hollow fiber membrane and having a hydrophilic thin layer formed at least on the inner surface of said hollow fiber membrane by the grafting of a hydrophilic compound through the agency of a gamma ray, a method for the cleaning blood and an apparatus therefor using the same.

6 Claims, 3 Drawing Sheets

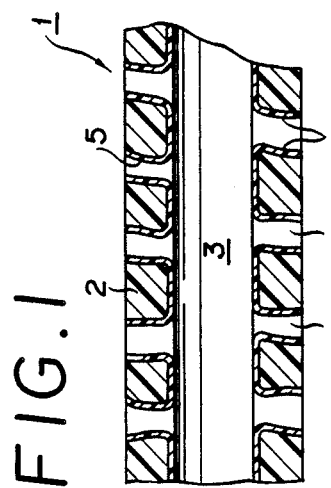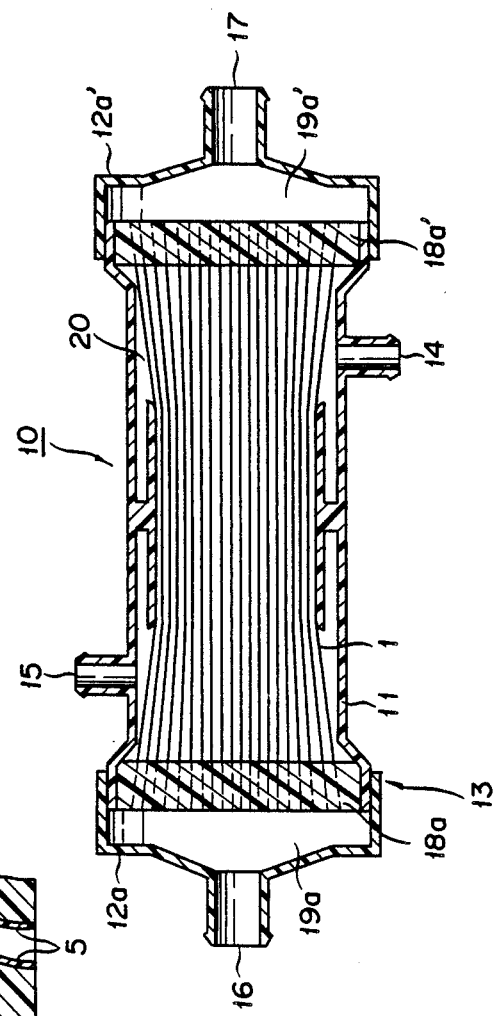

500
BLOOD CLEANING HOLLOW FIBER MEMBRANE, METHOD FOR CLEANING BLOOD, AND APPARATUS THEREFOR

BACKGROUND OF THE INVENTION

1. Field of the Invention:

This invention relates to a blood cleaning hollow fiber membrane, a method for cleaning blood, and an apparatus therefor. More particularly, it relates to a blood cleaning hollow fiber membrane to be used for removing from blood a protective liquid incorporated therein for permitting frozen storage of the blood, a method for cleaning blood, and an apparatus therefor.

2. Description of the Prior Art:

In recent years, the practice of componential transfusion which comprises fractionating a donor's blood so as to choose only elements necessary for a given patient and transfusing the chosen elements into the patient is taking the place of the practice of transfusing the so-called complete blood, i.e. the blood obtained from a donor in the form containing all the elements thereof. The componential transfusion have advantages that the burden on the circulatory system can be repressed and the immunological secondary reaction alleviated as compared with the complete-blood transfusion, that only necessary elements can be transfused in a large amount at a time and, therefore, even elements contained in small proportions in the complete blood can be expected to manifest their effects sufficiently, and that elements unnecessary for one patient may be effectively utilized for some other patient [Tanaka and Shimizu: Sogo Rinsho (comprehensive clinic), Vol. 35, No. 11 (1986)]. It nevertheless is still imperfect with respect to the preclusion of the two major secondary reactions, infection and sensitization, which are entrained by the operation of transfusion. Today, the infection of patients with hepatitis, AIDS, and ATLA or the sensitization particularly of infantile patients due to transfusion of affected blood has been arousing grave anxiety to the general public. The situation is urging perfection of a preventive measure effective in curbing the impact of transfusion of affected blood.

Recently, as a prospective way of solving the problem, the autoblood transfusion method which comprises transfusing into a patient the blood collected in advance from the patient himself has been attracting growing attention. The use of the patient's own blood is essentially incapable of causing such problems as infection with virus and sensitization mentioned above. By this method, even persons of very rare blood types can be assured that they have their blood ready for transfusion in case of an accident.

In accordance with this autoblood transfusion method, the blood taken from a person himself is fractionated into component elements and, as such, put to frozen storage. Even by the latest technical standard, the blood in its liquid state can be safely preserved for 42 days at most. The frozen storage enables such fractionated blood elements to be safely preserved semipermanently and permits establishment of a system of safe transfusion.

When the fractionated blood elements are put in their unmodified form to frozen storage, such elements as erythrocytes, leukocytes, and platelets are destined to be destroyed. For these component elements to be safely preserved in the frozen storage, they require incorporation of protective liquids therein. These protective liquids are variable with research organs engaging in the development thereof and of course with particular component elements to be protected. Most of them use glycerol and dimethyl sulfoxide as main components. When they are to be returned to the owner's body, they must be defrosted, diluted, and then cleaned to be freed of the protective liquids.

For the dilution and washing, a few methods have been already put to use such as, for example, a method which, in the case of a red blood corpuscle concentrate slowly frozen as mixed with Hagging's solution (containing 79% of glycerol, 8% of dextrose, 1% of fructose, and 0.3% of EDTA-disodium salt), for example, effects the dilution and washing by giving to the frozen concentrate mixture a first washing with 50% dextrose solution +5% fructose solution, then a second washing with 5% fructose solution, further a third washing again with 5% fructose solution, a fourth washing with a physiological saline solution, and thereafter resuspending the washed concentrate in the phyisological saline solution [Boston Massachusetts General Hospital (Hagging) and National Fukuoka Central Hospital (Sumida)] and a method which, in the case of a red blood corpuscle concentrate rapidly frozen as mixed with a Rowe solution (containing 28% of glycerol, 3% of mannitol, and 0.65% of sodium chloride), for example, effects the dilution and washing by subjecting this concentrate in its unmodified form to a first centrifugal sedimentation and discarding the supernatant, subjecting the residue of the first sedimentation to a second centrifugal sedimentation as mixed with 15% of mannitol and 0.45% of NaCl solution and discarding the resultant supernatant, subjecting the residue to a third and a fourth centrifugal sedimentation each as mixed with 0.9% NaCl solution and discarding the resultant supernatant, and finally resuspending the residue in a physiological saline solution [New York Blood Center (Rowe)].

Thus, the methods heretofore employed invariably effect the dilution and washing batchwise and necessitate either centrifugal sedimentation or centrifugal separation and involve a very complicated procedure. Moreover, they recover the component elements of blood with the efficiency hardly deserving any esteem.

An object of this invention, therefore, is to provide a blood cleaning hollow fiber membrane capable of facilitating the cleaning operation performed on frozen blood, a method for cleaning the blood, and an apparatus therefor.

Another object of this invention is to provide a blood cleaning hollow fiber membrane permitting germfree and continuous cleaning operation, a method for cleaning the blood, and an apparatus therefor.

A further object of this invention is to provide a blood cleaning hollow fiber membrane enabling component elements of blood to be recovered with high efficiency, a method for washing the blood, and an apparatus therefor.

SUMMARY OF THE INVENTION

The objects described above are accomplished by a blood cleaning hollow fiber membrane characterized by comprising a hydrophobic porous hollow fiber membrane and having a hydrophilic thin layer formed at least on the inner surface of the hollow fiber membrane by the grafting of a hydrophilic compound through the agency of a gamma ray.

This invention discloses a preferred embodiment of the blood cleaning hollow fiber membrane, wherein the hydrophilic compound is glycerol. This invention also discloses a preferred embodiment of the blood cleaning hollow fiber membrane, wherein the hydrophobic porous hollow fiber membrane is formed of one member selected from the group consisting of polyolefin type, polyester type, polyamide type, polyurethane type, poly(meth)acrylate type, poly(meth)acrylonitrile type, polysulfone type, and polyvinyl chloride type compounds and polymer blends thereof, preferably polypropylene. This invention further discloses a preferred embodiment of the blood cleaning hollow fiber membrane, wherein the inside diameter is in the range of 100 to 500 =m and the wall thickness in the range of 5 to 30 $\mu$m. This invention discloses a preferred embodiment of the blood cleaning hollow fiber membrane, wherein the average pore diameter is in the range of 0.01 to 6.5 $\mu$m and the void ratio is in the range of 30 to 75%.

The objects described above are also accomplished by a blood cleaning apparatus, produced by arranging inside a housing a multiplicity of blood cleaning hollow fiber membranes each comprising a hydrophobic porous hollow fiber membrane and having a hydrophilic thin layer formed at least on the inner surface of the hollow fiber membrane by the grafting of a hydrophilic compound through the agency of a gamma ray, causing the empty spaces inside the hollow fiber membranes to communicate with a blood inlet and a blood outlet disposed in the housing, and causing the empty spaces defined by the inner surface of the housing and the outer surface of the porous hollow fiber membranes to communicate with a cleaning liquid inlet and a cleaning liquid outlet disposed in the housing.

This invention discloses a preferred embodiment of the blood cleaning apparatus, which has been sterilized by a gamma ray. This invention discloses a preferred embodiment of the blood cleaning apparatus, wherein the hydrophilic compound is glycerol. This invention also disclcoses a preferred embodiment of the blood cleaning apparatus, wherein the hydrophobic porous hollow fiber membranes are each formed of one member selected from the group consisting of polyolefin type, polyester type, polyamide type, polyurethane type, poly(meth)acrylate type, poly(meth)acrylonitrile type, polysulfone type, and polyvinyl chloride type compounds and polymer blends thereof, preferably polypropylene. This invention further discloses a preferred embodiment of the blood cleaning apparatus, wherein the blood cleaning hollow fiber membranes each possess an inside diameter in the range of 100 to 500 $\mu$m and a wall thickness in the range of 5 to 30 $\mu$m. This invention discloses a preferred embodiment of the blood cleaning apparatus, wherein the blood cleaning hollow fiber membranes each possess an average pore diameter in the range of 0.01 to 6.5 $\mu$m and a void ratio in the range of 30 to 75%.

The objects described above are further accomplished by a method for the cleaning of freeze preserved blood, which method is characterized by using a plurality of blood cleaning apparatuses each constructed by arranging a multiplicity of porous hollow fiber membranes inside a housing, causing the empty spaces in the hollow fiber membranes to communicate with first fluid inlet and outlet provided in the housing thereby forming a first fluid passing space and causing the empty space defined by the inner surface of the housing and the outer surface of the porous hollow fiber membranes to communicate with second fluid inlet and fluid outlet thereby forming a second fluid passing space partitioned from the first fluid passing space, thereby enabling a plurality of steps of cleaning operation to be carried out continuously by serially connecting either the first fluid passing spaces or the second fluid passing spaces of the blood cleaning apparatuses thereby forming blood flow paths, arranging the connected blood flow paths substantially linearly, passing the blood subjected to cleaning through the linearly arranged blood flow paths, and meanwhile feeding mutually different or similar cleaning liquids through the remaining plurality of second or first fluid passing spaces.

This invention discloses a preferred embodiment of the method for cleaning the freeze preserved blood, wherein the blood is fed in the direction of gravity. This invention also discloses a preferred embodiment of the method for cleaning the freeze preserved blood, wherein the blood is fed in a direction opposite the direction of gravity. This invention further discloses a preferred embodiment of the method for cleaning the freeze preserved blood, wherein the porous hollow fiber membranes arranged inside the blood cleaning apparatuses each comprises a hydrophobic porous hollow fiber membrane and having a hydrophilic thin layer formed at least on the inner surface of the hollow fiber membrane by the grafting of a hydrophilic compound through the agency of a gamma ray.

The objects descirbed above are also accomplished by a method for the cleaning of freeze preserved blood, which method is characterized by using a plurality of blood cleaning apparatuses each constructed by arranging a multiplicity of porous hollow fiber membranes inside a housing, causing the empty spaces in the hollow fiber membranes to communicate with first fluid inlet and outlet provided in the housing thereby forming a first fluid passing space and causing the empty space defined by the inner surface of the housing and the outer surface of the porous hollow fiber membranes to communicate with second fluid inlet and fluid outlet thereby forming a second fluid passing space partitioned from the first fluid passing space, thereby enabling a plurality of steps of cleaning operation to be carried out continuously by serially connecting either the first fluid passing spaces or the second fluid passing spaces of the blood cleaning apparatuses thereby forming blood flow paths, arranging the connected blood flow paths substantially linearly, causing some of either the first fluid passing spaces or the second fluid passing spaces of the plurality of blood cleaning apparatuses forming part of the blood flow path to be disposed in the direction of gravity and the remainders thereof to be disposed in a direction opposite the direction of gravity in the continued blood flow paths, passing the blood subjected to cleaning through the linearly arranged blood flow paths, and meanwhile feeding mutually different or similar cleaning liquids through the remaining plurality of second or first fluid passing spaces.

This invention discloses a preferred embodiment of the method for cleaning the freeze preserved blood, wherein the porous hollow fiber membranes arranged inside the blood cleaning appratuses each comprises a hydrophobic porous hollow fiber memrane and having a hydrophilic thin layer formed at least on the inner surface of the hollow fiber membrane by the grafting of a hydrophilic compound through the agency of a gamma ray.

BRIEF DESCRIPTION OF THE DRAWINGS

FIG. 1 is a cross section illustrating in model a detailed construction of a blood cleaning hollow fiber membrane of the present invention, FIG. 2 is a schematic cross section illustrating the construction of a typical blood cleaning apparatus of the present invention.

EXPLANATION OF PREFERRED EMBODIMENT

Figure 3:
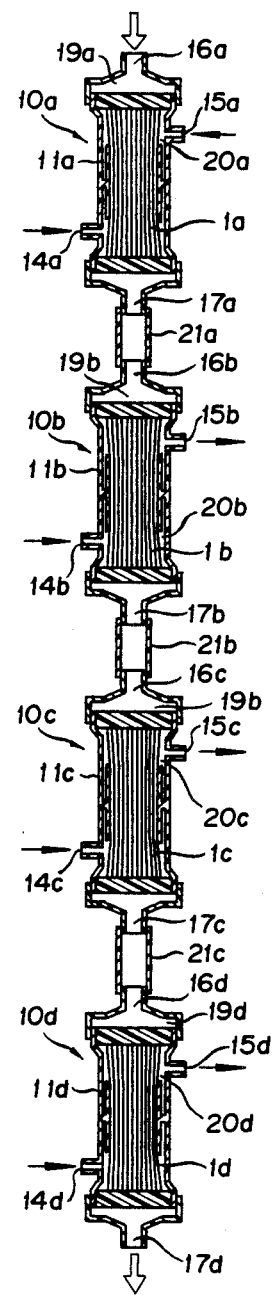
FIG. 3 is a model diagram illustrating a typical cleaning circuit for working the method for cleaning freeze preserved blood in accordance with the present invention.

The blood cleaning hollow fiber membrane of the present invention is characterized by comprising a hydrophobic porous hollow fiber membrane and having a hydrophilic thin layer formed at least on the inner surface of the hollow fiber membrane and the inner surface of pores in the hollow fiber membrane by the grafting of a hydrophilic compound through the agency of a gamma ray.

As a way of enabling the cleaning of freeze preserved blood in the frozen blood storage system to be carried out in a continuous process, we have conceived a method of cleaning by use of a porous hollow fiber membrane of the kind observed in the dialysis of blood with the artificial kidney. To be specific, this method comprises forming a cleaning apparatus having a multiplicity of porous hollow fiber membranes stowed in a housing and effecting the required cleaning of the preserved blood by passing the blood the empty spaces in the multiplicity of porous hollow fiber membranes and meanwhile passing a cleaning liquid in the empty space defined by the outer surfaces of the porous hollow fiber membranes and the inner surface of the housing thereby causing blood protecting liquid components such as glycerol contained the preserved blood to be removed from the preserved blood and passed through the hollow fiber membrane's into the cleaning liquid by virtue of difference in concentration. When a plurality of such cleaning appratuses are serially connected (by joining a blood outlet of one blood cleaning apparatus to a blood inlet of another blood cleaning apparatus thereby forming a continuous conduit through the blood flow paths of the plurality of blood cleaning appratuses), a plurality of steps of cleaning treatment can be carried out continuously in a closed system. When such hydrophilic porous hollow fiber membranes as cuprammonium regenerated celluolose membranes which have heretofore been used for the dialysis of blood are used in the cleaning treatment described above, however, the hydrophilic porous hollow fiber membranes are readily swelled with the water or the aqueous 5 to 10% glycerol solution which is kept filling the blood cleaning apparatuses until use for the purpose of shortening the priming time or upon contact with the preserved blood or the cleaning liquid. Thus, the pores in the porous hollow fiber membranes are occluded or contracted and the protecting liquid components such as glycerol contained in the preserved blood cannot be sufficiently removed by permeation. Further, these hydrophilic porous hollow fiber membranes are not fully satisfactory in terms of physical properties such as mechanical strength. We have drawn a conclusion that the hydrophilic porous hollow fiber membranes are not very suitable as hollow fiber membranes for blood cleaning.

After a diligent study, we have found that a hydrophilic thin layer is formed on at least the inner surface of a hydrophobic porous hollow fiber membrane and the inner surfaces of pores in the porous hollow fiber membrane when the hydrophobic porous hollow fiber membrane is filled in the empty space thereof with a hydrophilic compound and irradiated in that state to a gamma ray and that the hydrophilic porous hollow fiber membrane thus obtained possesses sufficient hydrophilicity and mechanical strength and, when used for the purpose of blood cleaning, avoids inducing the aforementioned problem of occlusion or contraction of pores by swelling, and exhibits outstanding permeation characteristics enough to permit thorough and efficient removal of such protecting liquid components as glycerol from the preserved blood. We have drawn thereupon a conclusion that the method which comprises disposing such hydrophobic porous hollow fiber membranes in a housing for a blood cleaning apparatus and subsequently filling the hydrophobic porous hollow fiber membranes in the empty spaces thereof with a hydrophilic compound and irradiating the hydrophobic porous hollow fiber membranes with a gamma ray as described above is highly desirable because the treatment is capable of converting the hydrophobic porous hollow fiber membranes into hydrophilic countertypes and, at the same time, effecting gamma-ray sterilization of the blood cleaning apparatus. This invention has been perfected as the result.

The method of this invention for the cleaning of freeze preserved blood comprises seriously connecting either first liquid passing spaces or second liquid passing spaces of a plurality of blood cleaning apparatuses each incorporating therein a multiplicity of porous hollow fiber membranes by joining thereby forming continuous blood flow paths and disposing these continuous blood flow paths substantially linearly and effecting the required cleaning of blood by passing the blood to be cleaned through the continuous blood flow paths and meantime feeding different or similar cleaning liquids to the plurality of second liquid passing spaces or first liquid passing spaces which are independent of each other.

The cleaning method of the present invention gives to the preserved blood which has been retrieved from the frozen blood storage system and then defrosted the required cleaning by use of porous hollow fiber membranes. To be more specific, the cleaning method of this invention comprises passing the preserved blood or the cleaning liquid through the empty spaces in the multiplicity of porous hollow fiber membranes (first liquid passing spaces) disposed in the blood cleaning apparatus of the description given above and meanwhile passing the cleaning liquid or the preserved blood through the empty space defined by the outer surfaces of the porous hollow fiber membranes and the inner surface of the housing (second liquid passing space) thereby causing such blood protecting liquid components as glycerol contained in the preserved blood to be removed from the preserved blood and passed through the hollow fiber membranes into the cleaning liquid by virtue of difference in concentration. Thus, the method of this invention enables the cleaning of the preserved blood by a simple, germfree, and efficient treatment without requiring such treatments as centrifugal sedimentation or centrifugal separation which are complicated and productive of adverse effects upon blood elements.

In the freeze preserving system for blood, since glycerol and other protective liquid components incorporated in the preserved blood and destined to be removed therefrom are contained in high concentrations and are numerous in kind, there arises the possibility that even when the blood cleaning apparatus to be employed has such porous hollow fiber membranes disposed as described therein, no efficient cleaning is obtained by using only one kind of cleaning liquid in one blood cleaning apparatus and no sufficient cleaning is attained by increasing the available length of the blood cleaning apparatus. In the method of this invention for cleaning the freeze preserved blood, since the plurality of blood cleaning apparatuses used therefor have their blood passing spaces (first liquid passing spaces and second liquid passing spaces) serially connected, the blood can be continuously given a plurality of germfree cleaning treatments sequentially through the blood cleaning apparatuses forming a closed system, specifically in such a manner that the blood, on being treated in the first blood cleaning apparatus, is continuously fed to the second blood cleaning apparatus without being expoed to the ambient air and subjected to the treatment in the second blood cleaning apparatus, and so on. In accordance with the method of this invention for treating the freeze preserved blood, since the individual blood cleaning apparatuses have independent paths for passing cleaning liquids, it is made possible to use different cleaning liquids in different blood cleaning apparatuses (though it is of course permissible to use similar cleaning liquids in different blood cleaning apparatuses). Thus, the cleaning treatments can be carried out efficiently.

Further, in the method of this invention for cleaning the freeze preserved blood, the empty spaces for passing the blood in the plurality of blood cleaning apparatuses are disposed substantially linearly. The flow of the blood through these cleaning paths, therefore, is retained substantially in a constant rate without entailing the possibility of exerting any burden on the blood elements. The damage possibly done to the blood elements during the cleaning treatment can be minimized as the result.

In another method of the present invention for cleaning the freeze preserved blood, a blood flow path is formed by serially connecting either first liquid passing spaces or second liquid passing spaces of a plurality of blood cleaning appratuses each provided with a multiplicity of porous hollow fiber membranes. In the continued blood flow path, some of the first liquid passing spaces or the second liquid passing spaces of a plurality of blood cleaning apparatuses participating in the formation of part of the blood flow path are disposed in the direction of gravity and some of the remaining liquid passing spaces are disposed in a direction opposite the direction of gravity. The blood subjected to cleaning is passed through the blood flow path constructed as described above. In the meantime, different or similar cleaning liquids are passed through the plurality of mutually independent second liquid passing spaces or first liquid passing spaces.

This method brings about functions in addition to the functions described above. Since some of the empty spaces for passing blood in the plurality of blood cleaning apparatuses are disposed in the direction of gravity and some of the others in a direction opposite the direction of gravity, the flow of blood through this path occurs in the direction equal to the direction of gravity in some of the blood cleaning apparatuses and in the direction opposite that of gravity in some of the remaining blood cleaning apparatuses. During the passage of the blood through this path, therefore, the apparent weights of such component elements of blood as red blood corpuscles, white blood corpuscles, and platelets contained in the blood under treatment are not fixed but are varied from one to another of the blood cleaning apparatuses. Surprisingly it has been demonstrated that efficient cleaning of the blood is accomplished by inducing this variation in the apparent weights of the component elements of blood.

Now, the present invention will be described more specifically below with reference to working embodiments.

FIG. 1 is a diagram illustrating in model the detailed construction of a hollow fiber membrane for cleaning blood in accordance with this invention. As illustrated in FIG. 1, a hollow fiber membrane 1 of this invention for cleaning blood is characterized by the fact that a hydrophilic thin layer 5 is formed at least on an inner surface 3 or a hydrophobic porous hollow fiber membrane 2 and on an inner surface 4 of pores by having hydrophilic compound grafted thereto through the agency of a gamma ray.

The hydrophobic porous hollow fiber membrane 1 to be used as a substrate for the hollow fiber membrane for cleaning blood according to this invention is not particularly critical. Various hydrophobic synthetic resins such as, for example, polyolefin type, polyester type, polyamide type, polyurethane type, poly(meth)acrylate type, poly(meth)acrylonitrile type, polysulfone type, and polyvinyl chloride type resins and polymer blends thereof are available. Among other types of hydrophobic synthetic resins mentioned above, those of the polyolefin type are particularly desirable in terms of resistance to gamma ray, mechanical strength, etc. Polypropylene is the best of all these synthetic resins. The method for producing the porous hollow fiber from such a hydrophobic synthetic resin is not particularly critical. The porous hollow fiber membrane can be produced by any of the conventional methods. A method which comprises melt spinning a given resin in the form of a hollow thread and subsequently stretching the hollow thread thermally thereby imparting porosity to the stretched hollow thread, a method which comprises mixing a polymer dope with a compound readily soluble in a solvent, melt spinning the resultant mixture into a hollow thread, and bringing the hollow thread into contact with a solvent thereby expelling the aforementioned compound by extraction and effecting impartation of porosity to the hollow thread, and a method which comprises mixing a polymer blend with a compound partially compatible with the polymer and readily soluble in a solvent, melt spinning the resultant mixture into a hollow thread, causing the hollow thread to contact a solvent, drying the hollow thread wet with the solvent, and stretching the dried hollow thread thereby imparting porosity to the hollow thread are available for the production of the porous hollow fiber membrane. More specifically, a method which comprises melt spinning polypropylene through a hollow fiber producing nozzle at a spinning temperature in the range of 210° to 270° C. at a draft ratio in the range of 180 to 600, subjecting the resultant hollow thread to a first heat treatment at a temperature not higher than 155° C., stretching the hot hollow thread at a ratio in the range of 30 to 200% at a temperature lower than 110° C., and thereafter subjecting the stretched hollow thread to a second heat treatment at a temperature exceeding the temperature of the first heat treatment and not exceeding 155° C. (Japanese Patent Publication SHO 56(1981)-52,123), a method which comprises mixing a stretchable polymer with a compound partially compatible with the polymer and readily soluble in a solvent, melt spinning the resultant mixture into a hollow thread, treating the hollow thread with a solvent, drying the hollow thread, and uniaxially or biaxially stretching the dried hollow thread at a ratio in the range of 50 to 1,500% thereby imparting porosity to the hollow thread (Japanese Patent Publication SHO 57(1982)-20,970), and a method which comprises mixing a polyolefin, an organic filler uniformly dispersible in the polyolefin while the polyolefin is in a molten state and easily soluble in an extractant to be used, and optionally a crystal seed forming agent, melting the resultant mixture, discharging the molten mixture through an annular spinning nozzle, cooling and solidifying the resultant hollow thread by contact thereof with a cooling and solidifying liquid incapable of dissolving the polyolefin, and causing the cooled and solidified hollow thread to contact the extractant thereby expelling the organic filler therefrom by extraction (Japanese Patent Laid-Opens SHO 61(1986)-90,703 and SHO 61(1986)-90,705) may be cited, for example. The pore diameter, the void ratio, and other constructional details of the hydrophobic porous hollow fiber membrane produced as described above are determined by the kind of the preserved blood to be treated. When the preserved blood is a red blood corpuscle concentrate, for example, the hydrophobic porous hollow fiber membrane is desired to have an average pore diameter in the range of 0.01 to 6.5 $\mu$m, preferably 1.0 to 6.0 $\mu$m, and a void ratio in the range of 30 to 75%, preferably 60 to 75%, though these ranges hinge in some measure on the kind of the hydrophobic synthetic resin selected for the hollow fiber membrane and the kind of method for the production thereof. If the average pore diameter is less than 0.01 $\mu$m, there arises the possibility that the glycerol and other protective liqud components contained in the preserved blood are not sufficiently passed and the treatment of the blood require an unduly long time. Conversely, if the average pore diameter exceeds 6.5 $\mu$m, there ensues the possibility that even the red blood corpuscles are suffered to permeate the membrane during the course of the cleaning treatment. When the preserved blood to be treated is a platelet fraction, the average pore diameter is desired to be approximately in the range of 0.01 to 1.5 $\mu$m, preferably 1.0 to 1.3 $\mu$m. When the preserved blood to be treated is a white blood corpuscle fraction, the average pore diameter is desired to be approximately in the ragne of 0.01 to 12.0 $\mu$m, preferably 1.0 to 10.0 $\mu$m. The efficiency of the blood treatment is not sufficient if the void ratio is less than 30%. If the void ratio exceeds 75%, the possibility arises that the mechanical strength of the hollow fiber membrane is too low for the membrane to be practicable. In terms of permeation property, mechanical strength, and volume property which counts when the hollow fiber membrane is used in the assembly of a blood cleaning apparatus as a module, the blood cleaning hollow fiber membrane is desired to possess an inside diameter in the range of 100 to 500 $\mu$m, preferably 200 to 300 $\mu$m, and a wall thickness in the range of 5 to 30 $\mu$m, preferably 8 to 15 $\mu$m.

As regards the kind of the hydrophilic compound which is grafted through the agency of a gamma ray at least on the inner surface 3 of the hydrophobic hollow fiber membrane 2 and on the inner surface 4 of the pores, no particular limits are imposed except for the sole requirement that the compound should exhibit high hydrophilicity, and desirably possess high physiological safety. The hydrophilic compounds answering the description include water-soluble alcohols such as methanol, ethanol, and glycerol, low molecular saccharides such as fructose, dextrose, and mannitol, water-soluble amino acids such as alanine, arginine, and cysteine, dicarboxylic acids such as oxalic acid, malonic acid, and succinic acid, ketoacetic acids such as glyoxilic acid, pyruvic acid, and acetoacetic acid, hydroxylic acids such as glycolic acid, lactic acid, and alpha-hydroxyacetic acid, unsaturated carbonyl compounds such as acrylic acid, maleic acid, and methacrylic acid, and sodium and potassium salts thereof, for example. Among other hydrophobic compounds mentioned above, glycerol is particularly desirable. When glycerol is selected, it is desired to be used in the form of an aqueous solution which containes glycerol in a concentration in the range of 5 to 10%, though it may be in the form of a concentrated glycerol solution.

The formation of the hydrophilic thin layer 5 of such a hydrophilic compound as described above on the inner surface 3 of the hydrophobic porous hollow fiber membrane 2 and on the inner surface 4 of the pores may be accomplished by filling the inner empty space of the hydrophobic porous hollow fiber membrane 2 with the hydrophilic compound and exposing the hydrophobic porous hollow fiber membrane to the gamma ray. This irradiation of the gamma ray is desired to be made to a dosage approximately in the range of 0.1 to 25 Mrad, preferably 2.5 to 10 Mrad. After the exposure to the gamma ray, the blood cleaning hollow fiber membrane 1 aimed at is obtained by discharging from the inenr empty space of the hydrophobic porous fiber membrane 2 the excess hydrophilic compound which has escaped being grafted to the hydrophobic porous membrane 2 and thoroughly washing the residual hydrophilic compound adhering to the inner empty space of the hydrophobic porous membrane 2 as with germfree distilled water or physiological saline solution. When the blood cleaning hollow fiber membrane of the present invention is to be used as in a blood cleaning apparatus, the procedure of first incorporating the hydrophobic porous hollow fiber membrane 2 in the blood cleaning apparatus, then filling the membrane with the hydrophilic compound, and thereafter exposing the membrane 2 per se to the gamma ray proves an immense advantage because this irradiation of the gamma ray fulfils the dual role of grafting the compound to the membrane 2 and sterilizing the blood cleaning apparatus.

Since the hydrophilic thin layer 5 is formed, as described above, by the hydrophilic compound of the quality described above being grafted through the agency of the gamma ray on the inner surface 3 of the hydrophobic porous fiber membrane 2 and on the inner surface 4 of the pores in the membrane 2, it is capable of imparting ample hydrophilicity to the porous hollow fiber membrane and yet is very thin and, even in a wet state, is substantially incapable of altering the texture possessed by the hydrophobic porous hollow fiber membrane and, therefore, is capable of manifesting a stable permeation property.

The blood cleaning apparatus of this invention is formed by arranging a multiplicity of such blood cleaning hollow fiber membranes as described above in a housing, causing the inner empty spaces of the hollow fiber membranes to communicate with a blood inlet and a blood outlet disposed in the housing, and meanwhile causing the empty space defined by the inner surface of the housing and the outer surfaces of the porous hollow fiber membranes to communicate with a cleaning liquid inlet and a cleaning liquid outlet. The blood cleaning apparatus constructed as described above effects desired cleaning of the preserved blood by passing the preserved blood through the empty spaces inside the hollow fiber membranes and the cleaning liquid outside the hollow fiber membranes thereby enabling the glycerol and other protective liquid components contained in the preserved blood to be passed through the hollow fiber membranes into the cleaning liquid by virtue of difference in concentration.

FIG. 2 is a shematic cross section illustrating the construction of a typical blood cleaning apparatus embodying the present invention. A blood cleaning apparatus 10 of the present embodiment illustrated in FIG. 2 is provided with a housing 13 which is composed of a cylindrical housing body 11 open at the opposite terminal parts and a lid 12a and a lid 12a' watertightly fitted into the opposite terminal open parts of the housing body 11. This housing body 11 is provided near one terminal part thereof with a cleaning liquid inlet 14 and near the other terminal part thereof with a cleaning liquid outlet 15. The lid 12a is provided therein with a blood inlet 16 and the lid 12a' similarly with a blood outlet 17. In the inner empty space of the housing 13, a multiplicity, approximately on the order of 10,000, blood cleaning hollow fiber membranes of the description given above are disposed as mutually separated along the axial direction of the housing 13. The opposite end parts of the blood cleaning hollow fiber membranes 1 are supported fast on the housing body 13 through the medium of diaphragms 18a, 18a' formed of a potting agent so placed as to fill the opposite terminal parts of the housing body 13 without occluding the openings of the blood cleaning hollow fiber membranes 1. Further, the diaphragms 18a, 18a' partition the inner empty space of the housing 13 into three portions. Inside the inner empty space of the housing 13, there are consequently formed a blood passing space defined by the inner surface of the housing body 11 and the diaphragm 18a and adapted to communicate with the blood inlet 16 and the inner empty spaces of the blood cleaning hollow fiber membranes 1, a cleaning liquid passing space defined by the inner surface of the housing body 11, the outer surfaces of the blood cleaning hollow fiber membranes 1, and the diaphragms 18a, 18a' and adapted to communicate with the cleaning liquid inlet 14 and the cleaning liquid outlet 15, and a blood passing space 19b defined by the inner surface of the housing body 11 and the diaphragm 18' and adapted to communicate with the blood outlet 17 and the inner empty spaces of the blood cleaning hollow fiber membranes 1. Thus, the diaphragms 18a, 18a' fulfil the important function of isolating the interior of the blood cleaning hollow fiber membranes from the exterior thereof. Generally, these diaphragms 18a, 18a' are formed by casting polyurethane, silicone, or epoxy resin by the centrifugal method on the opposite inner surfaces of the housing body 11 and allowing the cast layers of the resin to set.

The blood cleaning apparatus constructed as described above is subjected to a sterilizing treatment prior to use. Desirably, this sterilization can be effected by the autoclave method or the gamma ray method. Particularly, the procedure which comprises first incorporating the hydrophobic hollow fiber membranes destined to form matrices of the blood cleaning hollow fiber membranes in the blood cleaning apparatus, then filling the inner empty spaces of the hydrophobic porous hollow fiber membranes with the hydrophilic compound, and thereafter exposing hydrophobic porous hollow fiber membranes with the gamma ray thereby forming a hydrophilic thin layer on the inner surfaces of the hydrophobic porous hollow fiber membranes and the inner surfaces of the pores is desirable because the gamma ray plays the dual role of grafting the hydrophilic compound onto the hydrophobic porous hollow fiber membranes and sterilizing the whole blood cleaning apparatus at the same time. This hydrophilic thin layer is not altered but is enabled to manifest a stable permeation property.

In the method of this invention for cleaning the freeze preserved blood, a plurality of blood cleaning apparatuses 10 each constructed as described above are joined in such a manner that the first liquid passing spaces 19 of second liquid passing spaces 20 severally of the individual blood cleaning apparatuses 10 are serailly connected to give rise to a continuous cleaning line forming a blood flow path running through the individual blood cleaning apparatuses.

In a cleaning line illustrated in FIG. 3, for example, four blood cleaning apparatuses 10 each constructed as illustrated in FIG. 2 are joined by connecting the first liquid inlet 17a of the first blood cleaning apparatus 10a to the first liquid inlet 16b of the second blood cleaning apparatus 10b with a connecting tube 21a made of a flexible resin such as, for example, polypropylene or polyvinyl chloride, and then similarly connecting the first liquid outlet 17b of inlet 16c of the third blood cleaning apparatus 10c and the first liquid outlet 17c of the third blood cleaning apparatus to the first liquid inlet 16d of the fourth blood cleaning apparatus 10d thereby giving rise to a blood flow path running continuously through the first liquid passing space 19a of the first blood cleaning apparatus 10a, the first liquid passing space 19a of the second blood cleaning apparatus 10b, the first liquid passing space 19c of the third blood cleaning apparatus 10c, and the first liquid passing space 19d of the fourth blood cleaning apparatus 10d. In contrast, the second liquid passing spaces 20a, 20b, 20c, and 20d respectively of the blood cleaning apparatuses 10a, 10b, 10c, and 10d maintain independence and severally constitute themselves four independent cleaning liquid flow paths. In the embodiment illustrated in FIG. 3, the blood cleaning apparatuses 10a, 10b, 10c, and 10d are depicted as having their respective first liquid passing spaces 19a, 19a', 19b, 19b', 19c, 19c', 19d, and 19d' joined to form a continuous flow path therethrough and permit passage of blood inside the porous hollow membranes 1a, 1b, 1c, and 1d. Optionally, the blood cleaning appratuses 10a, 10b, 10c, and 10d may be so joined as to form a continuous flow path through their second liquid passing spaces 20a, 20b, 20c, and 20d and permit passage of blood outside the porous hollow fiber membranes. It is naturally permissible to increase or decrease the number of blood cleaning apparatuses as occasion demands.

In the method of the present invention for cleaning the freeze preserved blood, the blood flow paths connected to complete the cleaning line as described above are disposed substantially linearly. This statement is not meant to be very strict. The disposition of these blood flow paths in nearly one same direction substantially throughout the total length thereof suffices so long as they are not forced to bend in an entirely opposite direction. These blood flow paths are required to be disposed so that the gravity acts equally on the blood flowing therethrough. So long as they satisfy the requirement, they may be disposed downwardly (for the blood to flow in the direction of gravity) or upwardly (for the blood to flow in the direction opposite that of gravity) in the vertical direction or lateralay in the horizontal direction.

The cleaning operation which comprises a plurality of treatments can be carried out continuously by passing the blood to be cleaned through the blood flow paths so disposed as to form a continuous cleaning line as described above and passing different or similar cleaning liquids through the plurality of independent cleaning liquid flow paths (namely the second liquid passing space or first liquid passing spaces left unconnected). To describe this operation more specifically with reference to the embodiment illustrated in FIG. 1, the entire cleaning line is sterilized as by the autoclave method or the gamma ray method and it is then primed by passing physiological saline solution through the first liquid inlet 16a of the first blood cleaning apparatus 10a before the cleaning operation is started. Then, prescribed cleaning liquids are passed via the second liquid inlets 14a, 14b, 14c, and 14d of the blood cleaning apparatuses 10a, 10b, 10c, and 10d into the second liquid passing spaces 20a, 20b, 20c, and 20d and discharged via the second liquid outlets 15, 15b, 15c, and 15d. The cleaning liquids to be used in the blood cleaning apparatuses 10a, 10b, 10c, and 10d may be different from or similar to each other as occasion demands. When the flow volumes of the cleaning liquids being passed through the second liquid passing spaces 20a, 20b, 20c, and 20d of the blood cleaning apparatuses 10a, 10b, 10c, and 10d reach the prescribed constant levels within the range of 10 ml to 50 liters/min, preferably 100 ml to 5 liters/min, for example, the preserved blood defrosted in advance is fed via the first liquid inlet 16a of the first blood cleaning apparatus 10a into the blood flow path at a prescribed flow volume in the range of 10 to 2,000 ml/min, preferably 20 to 1,500 ml/min. The blood brought into the blood flow path, while flowing through the inner empty spaces of the porous hollow fiber membranes in the first liquid passing space 19a of the first blood cleaning apparatus 10a, is depleted of a prescribed protective liquid component to a prescribed proportion by the permeation of the liquid component through the porous hollow fiber membranes 1a into the first cleaning liquid being passed through the second liquid passing space 20a owing to the difference in concnetration. The blood is then forwarded into the first liquid passing space 19b of the second blood cleaning apparatus 10b and, while flowing through the inner empty spaces of the porous hollow fiber membranes within the first liquid passing space 19b, is depleted a prescribed remaining protective liquid component to a prescribed proportion by the permeation of the liquid component through the porous hollow fiber membranes 1b into the second cleaning liquid being passed through the second liquid passing space 20b owing to the difference in concentration. The blood is subsequently forwarded to the second liquid passing space 19b of the third blood cleaning apparatus 10c. Similarly in the third blood cleaning apparatus 10c and the four blood cleaning apparatus 10d, the remaining protective liquid components are removed by permeation. The blood which has been completely depleted of the protective liquid components through the series of four cleaning treatments is recovered via the first liquid outlet 17d of the fourth blood cleaning apparatus 10d and then put to use for transfusion.

In yet another method of the present invention for cleaning the freeze preserved blood, a plurality of blood cleaning apparatuses 10 each constructed as described above are so connected that either the first liquid passing spaces 15 or the second liquid passing spaces 18 of the individual blood cleaning apparatuses 10 are serially connected to give rise to a continuous cleaning line forming a blood flow path running through the blood cleaning appratuses 10.

In a cleaning line illustrated in FIG. 3, for example, four blood cleaning apparatuses 10 each constructed as illustrated in FIG. 2 are joined by connecting the first liquid outlet 17a of the first blood cleaning apparatus 10a to the first liquid inlet 16b of the second blood cleaning apparatus 10b with a connecting tube 21a made of a flexible resin such as, for example, polypropylene or polyvinyl chloride, and then similarly conencting the first liquid outlet 17b of the second blood cleaning apparatus 10b to the first liquid inlet 16c of the third blood cleaning apparatus 10c and the first liquid outlet 10c of the third blood cleaning apparatus 10c to the first liquid inlet 16d of the fourth blood cleaning apparatus 10d thereby giving rise to a blood flow path running continuously through the first liquid passing space 19a of the first blood cleaning apparatus 10a, the first liquid passing space 19b of the second blood cleaning apparatus 10b, the first liquid passing space 19c of the third blood cleaning apparatus 10c, and the first liquid passing space 19d of the fourth blood cleaning apparatus 10d. In contrast, the second liquid passing spaces 20a, 20b, 20c, and 20d respectively of the blood cleaning apparatuses 10a, 10b, 10c, and 10d maintain independence and severaly constitute themselves four independent cleaning liquid flow paths. In the embodiment illustrated in FIG. 4, the blood cleaning apparatuses 10a, 10b, 10c, and 10d are depicted as having their respective first liquid passing spaces 19a, 19b, 19c, and 19d joined to permit passage of blood inside the porous hollow fiber membranes 12. Optionally, the blood cleaning apparatuses 10a, 10b, 10c, and 10d may be so joined as to form a continuous flow path through their second liuqid passing spaces 20a, 20b, 20c, and 20d and permit passage of blood outside the porous hollow fiber membranes. It is naturally permissible to increase or decrease the number of blood cleaning apparatuses as occasion demands.

In the method of the present invention for cleaning the freeze preserved blood, the blood flow paths connected to complete the cleaning line as described above are disposed in such a manner that some of either the first liquid passing spaces or the second liquid passing spaces of the plurality of blood cleaning apparatuses forming part of the blood flow paths are arranged in the direction of gravity and the remainders thereof in a direction opposite the direction of gravity. This statement concerning the arrangement of the blood flow paths is not meant to be very strict. It is tolerable for the blood flow paths to be so disposed that some of the plurality of blood cleaning apparatuses are substantially reversed relative to the remainders thereof. In the blood flow paths, the ratio of the number of those of the first liquid passing spaces or the second liquid passing spaces of the plurality of blood cleaning apparatuses forming part of the blood flow paths which are disposed in the direction of gravity to the number of those which are disposed in the direciton opposite the direction of gravity is not specifically critical. The occurrence of at least one such liquid passing space in either of the two directions under discussion suffices. The occurrence of nearly equal number of such liquid passing spaces in both of the directions is desirable. Further, the order in which the dispositions in the two direction occur is not critical at all. For example, first several of the liquid passing spaces may be disposed in the direction of gravity and the remaining several thereof in the direction opposite the direction of gravity. Otherwise, the liquid passing spaces may be disposed altrnately in the direction of gravity and in the direction opposite the direction of gravity.

The cleaning operation which comprises a plurality of treatments can be carried out continuously by passing the blood to be cleaned through the blood flow paths so disposed as to form a continuous cleaning line as described above and passing different or similar cleaning liquids through the plurality of independent cleaning liquid flow paths (namely the second liquid passing spaces left unconnected). To describe this operation more specifically with reference to the embodiment illustrated in FIG. 4, the entire cleaning line is sterilized as by the autocalve method or the gamma ray method and it is then primed by passing physiological saline solution through the first liquid inlet 16a of the first blood cleaning apparatus 10a before the cleaning operation is started. Then, prescribed cleaning liquids are passed via the second liquid inlets 14a, 14b, 14c, and 14d of the blood cleaning apparatuses 10a, 10b, 10c, and 10d into the second liquid passing spaces 20a, 20b, 20c, and 20d and discharged via the second liquid outlets 15a, 15b, 15c, and 15d. The cleaning liquids to be used in the blood cleaning apparatuses 10a, 10b, 10c, and 10d may be different from or similar to each other as occasion demands. When the flow volumes of the cleaning liquids being passed through the second liquid passing spaces 20a, 20b, 20c, and 20d of the blood cleaning apparatuses 10a, 10b, 10c, and 10d reach the prescribed constant levels within the range of 10 ml to 50 liters/min, preferably 100 ml to 5 liters/min, for example, the preserved blood defrosted in advance is fed via the first liquid inlet 16a of the first blood cleaning apparatus 10a into the blood flow path at a prescribed flow volume in the range of 10 to 2,000 ml/min, preferably 20 to 1,500 ml/min. The blood brought into the blood flow path, while flowing through the inner empty spaces of the porous hollow fiber membranes in the first liquid passing space 19a of the first blood cleaning apparatus 10a, is depleted of a prescribed protective liquid component to a prescribed proportion by the permeation of the liquid component through the porous hollow fiber membranes 1a into the first cleaning liquid being passed through the second liquid passing space 20a owing to the difference in concentration. The blood is then forwarded into the first liquid passing space 19b of the second blood cleaning apparatus 10b and, while flowing through the inner empty spaces of the porous hollow fiber membranes within the first liquid passing space 19b, is depleted a prescribed remaining protective liquid component to a prescribed prorportion by the permeation of the liquid component through the porous hollow fiber membranes 1b into the second cleaning liquid being passed through the second liquid passing space 20b owing to the difference in concentration. The blood is subsequently forwarded to the second liquid passing space 19c of the third blood cleaning apparatus 10c. Similarly in the third blood cleaning apparatus 10c and the four blood cleaning apparatus 10d, the remaining protective liquid components are removed by permeation. The blood which has been completely depleted of the protective liquid components through the series of four cleaning treatments is recovered via the first liquid outlet 17d of the fourth blood cleaning apparatus 10d and the put to use for transfusion.

The method of the present invention for cleaning the freeze preserved blood is worked out as described above. By modifying the cleaning liquids and the pore properties of the porous hollow fiber membranes to be used in accordance with the kinds of blood elements preserved and the kinds of protective liquid components to be incorporated, the method of this invention can be applied to the cleaning of various component elements of blood such as red blood corpuscle fraction, platelet fraction, white blood corpuscle fraction, (or lymphocyte fraction and glanulocyte fraction), and bone marrow fraction after such component elements are defrosted.

Now, the present invention will be described more specifically below with reference to working examples.

Example 1

In a cylindrical housing 11 of a blood cleaning apparatus 10 constructed as illustrated in FIG. 2, 10,000 porous hollow fiber membranes (average pore diameter 1.0 $\mu$m and void ratio 70%) 200 $\mu$m in inside diameter and 10 $\mu$m in wall thickness were disposed. The opposite end parts of these hollow fiber membranes were fixed in place with a potting material of polyurethane to fasten the porous hollow fiber membranes 12 inside the housing body 11 and give rise to a blood cleaning apparatus 10 having an available length of 230 mm and an available membrane surface of 1.6 m². Four blood cleaning apparatuses of the same construction were produced. Then, the first liquid outlets 17a, 17b, and 17c, of one apparatus were connected to the first liquid inlets 16b, 16c, and 16d of another apparatus with connection tubes 21a, 21b, and 21c made of polyethylene, to produce a cleaning line in which te first liquid passing spaces 19a, 19b, 19c, and 19d of the four blood cleaning apparatuses were serially connected. Glycerol was fed through the first liquid inlet 16a of the first blood cleaning apparatus 10a until the inner empty spaces of the porous hollow fiber membranes in the blood cleaning apparatuses 10a, 10b, 10c, and 10d were filled to capacity with the glycerol. The cleaning line so prepared was irradiated with a gamma ray to a dosage of 8 Mrad. After the exposure to the gamma ray, the cleaning line was purged of the glycerol and further cleaned thoroughly with germfree physiological saline solution to expel the residual glycerol adhering to the hollow fiber membranes. (In another test run, the blood cleaning apparatuses 10a, 10b, 10c, and 10d were filled with glycerol and, with the first liquid inlets 16a, 16b, 16c, and 16d, the first liquid outlets 17a, 17b, 17c, and 17d, the second liquid inlets 14a, 14b, 14c, and 14d, and the second liquid outlets 15a, 15b, 15c, and 15d sealed each with a cap, the blood cleaning apparatuses 10a, 10b, 10c, and 10d were irradiated with the gamma ray to a dosage of 8 Mrad for impartation of hydrophilicity and then incorporated in a germfree state in the housing body 11 as illustrated in FIG. 3.)

By use of the cleaning line treated as described above, a preserved blood was given a cleaning treatment. A red blood corpuscle concentrate contianing an equal volume of Hagging solution (containing 79% of glycerol, 8% of dextrose, 1% of fructose, and 0.3% of EDTA-disodium salt) and preserved at −85° C. was prepared as a sample to be cleaned and was defrosted at 40° C. In the meantime, the cleaning line was disposed so that the first blood cleaning apparatus 10a through the fourth blood cleaning apparatus 10d were positioned sequentially downwardly and substantially linearly in the vertical direction. Then, the whole cleaning line was primed with germfree physiological saline solution. Through the second liquid inlets 14a, 14b, 14c, and 14d of the blood cleaning appartuses 10a, 10b, 10c, and 10d, the cleaning liquids indicated in Table 1 were fed at a fixed flow rate of 500 ml/min into the second liquid passing spaces 20a, 20b, 20c, and 20d and continuously discharged via the second liquid outlets 15a, 15b, 15c, and 15d. After the flow rate of the cleaning liquids had reached a constant level, 400 ml of the defrosted blood was passed at a flow rate of 100 ml/min. through the first liquid inlet 16a of the first blood cleaning apparatus 10a into the cleaning line. The blood cleaned by passage through the cleaning line and released from the first liquid outlet 14d of the fourth blood cleaning apparatus 10d was collected. This cleaning treatment consumed 4.5 minutes. By taking counts of red blood corpuscles of the sample before and after the treatment, the recovery ratio of red blood corpuscles was found to be 95%. The cleaned blood was found to contain 0.1 ppm of glyceol, indicating the treatment effected substantially complete removal of glycerol.

TABLE 1

| | Cleaning liquid |
|---|---|
| First blood cleaning apparatus | 50% dextrose + 5% fructose solution |
| Second blood cleaning apparatus | 5% fructose solution |
| Third blood cleaning apparatus | 5% fructose solution |
| Fourth blood cleaning apparatus | Physiological saline solution |

Example 2

Figure 4:
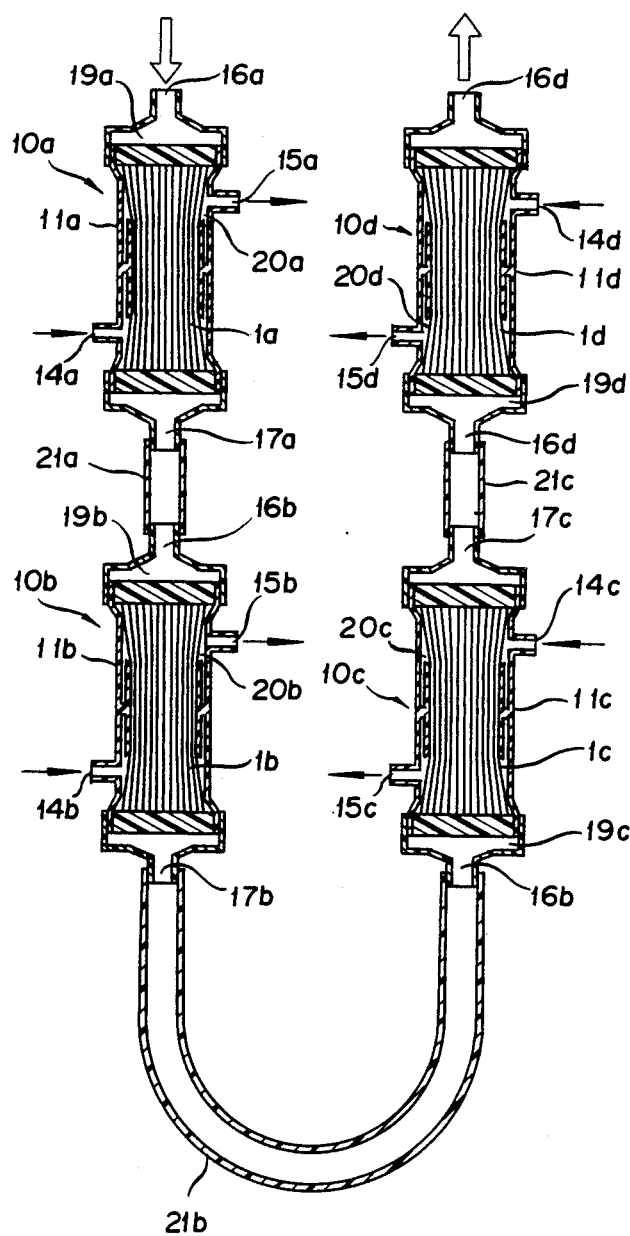
FIG. 4 is a model diagram illustrating another typical cleaning circuit for working the method for cleaning freeze preserved blood in accordacne with the present invention.

The same for blood cleaning apparatuses 10 that were used in Example 1 were joined in such a manner as illustrated in FIG. 4 that the first liquid outlets 17a, 17b, and 17c of one apparatus were connected to the first liquid inlets 16b, 16c, and 16d of another apparatus with connection tubes 21a made of polyethylene to complete a cleaning line having the first liquid passing spaces 19a, 19b, 19c, and 19d of the four blood cleaning apparatuses connected serially. Through the first liquid inlet 16a of the first blood cleaning apparatus 10a in the cleaning line, glycerol was fed until the inner empty spaces of the porous hollow fiber membranes 1 inside the blood cleaning apparatuses 10a, 10b, 10c, and 10d were filled to capacity with the glycerol. The whole cleaning line in the resultant state was irradiated with a gamma ray to a dosage of 8 Mrad. After exposure to the gamma ray, the cleaning line was depleted of the glycerol and was further purged throughly with germfree physiological saline solution to expel the residual glycerol adhering to the hollow fiber membranes. (In another test run, the blood cleaning apparatuses 10a, 10b, 10c, and 10d were filled with glycerol and, with the first liquid inlts 16a, 16b, 16c, and 16d, the first liquid outlets 17a, 17b, 17c, and 17d, the second liquid inlets 14a, 14b, 14c, and 14d, and the second liquid outlets 15a, 15b, 15c, and 15d sealed each with a cap, the blood cleaning apparatuses 10a, 10b, 10c, and 10d were irradiates with a gamma ray to a dosage of 8 Mrad for impartation of hydrophilicity, and were assembled in a germfree state as illustrated in FIG. 4).

By use of the cleaning line treated as described above, a preserved blood was given a cleaning treatment. A red blood corpuscle concentrate containing an equal volume of Hagging solution (containing 79% of glycerol, 8% of dextrose, 1% of fructose, and 0.3% of EDTA-disodium salt) and preserved at −85° C. was prepared and defrosted at 40° C. In the meantime, the cleaning line was disposed in such a manner as illustrated in FIG. 4 that the first liquid passing space 19a of the first blood cleaning apparatus 10a and the first liquid passing space 19b of the second blood cleaning apparatus 10b were arranged in the direction of gravity and the first liquid passing space 19c of the third blood cleaning apparatus 10c and the first liquid passing space 19d of the fourth blood cleaning apparatus 10d in the direction opposite the direction of gravity. Then, the whole cleaning line was primed with germfree physiological saline solution. Then, the cleaning liquids indicated in Table 2 were fed at a fixed flow rate of 500 ml/min through the second liquid inlets 14a, 14b, 14c, and 14d of the blood cleaning apparatuses 10a, 10b, 10c, and 10d in the cleaning line into the second liquid passing spaces 20a, 20b, 20c, and 20d and continuously discharged via the second liquid outlets 15a, 15b, 15c, and 15d. After the flow rate of the cleaning liquids had reached a constant level, 400 ml of the defrosted blood was fed at a flow rate of 50 ml/min through the first liquid inlet 13a of the first blood cleaning apparatus 10a into the cleaning line. The blood cleaned by passage through the cleaning line and released via the first liquid outlet 17d of the fourth blood cleaning apparatus was collected. The cleaning treatment consumed 10 minutes. By taking counts of red blood corpuscles before and after the cleaning treatment, the recovery ratio of red blood corpuscles was found to be 98%. The blood resulting from the cleaning treatment was found to contain 0.1 ppm of glycerol, indicating that the cleaning treatment effected substantially complete removal of glycerol.

TABLE 2

| | Cleaning liquid |
|---|---|
| First blood cleaning apparatus | 50% dextrose + 5% fructose solution |
| Second blood cleaning apparatus | 5% fructose solution |
| Third blood cleaning apparatus | 5% fructose solution |
| Fourth blood cleaning apparatus | Physiological saline solution |

As described above, the present invention is directed to a blood cleaning quality hollow fiber membrane which is characterized by comprising a hydrophobic porous hollow fiber membrane and having a hydrophilic thin layer formed at least on the inner surface of the hollow fiber membrane by the grafting of a hydrophilic compound through the agency of a gamma ray. This blood cleaning quality hollow fiber membrane, therefore, is amply rich in hydrophilicity and permeability to water. Since the hydrophilicity is imparted thereto by the very thin hydrophilic layer, the membrane cannot entail the disadvantage that when it is wetted, the properties of the membrane are altered. Further it excels in terms of mechanical strength When a blood cleaning apparatus incorporating therein a multiplicity of such blood cleaning quality hollow fiber membranes is used as in cleaning a freeze preserved blood, for example, glycerol and other protective liquid components contained in the freeze preserved blood can be efficiently and readily removed the blood.

This invention is also directed to a blood cleaning apparatus, produced by arranging inside a housing a multiplicity of blood cleaning hollow fiber membranes each comprising a hydrophobic porous hollow fiber membrane and having a hydrophilic thin layer formed at least on the inner surface of the hollow fiber membrane by the grafting of a hydrophilic compound through the agency of a gamma ray, causing the empty spaces inside the hollow fiber membranes to communicate with a blood inlet and blood outlet disposed in the housing, and causing the empty spaces defined by the inner surface of the housing and the outer surface of the porous hollow fiber membranes to communicate with a cleaning liquid inlet and a cleaning liquid outlet disposed in the housing. Since this blood cleaning apparatus effects a cleaning operation on the freeze preserved blood by virtue of the multiplicity of hollow fiber membranes possessing high desirable properties, it cleans the blood very efficiently and recovers the blood elements in a very high recovery ratio. When a plurality of such blood cleaning apparatuses are interconnected, the operation of cleaning the freeze preserved blood which has heretofore been carried out batchwise can be performed continuously in a germfree state. Thus, they contributes a great deal to the growth of the frozen storage system for blood. When the treatment for imparting hydrophilicity by the irradiation with a gamma ray to the inner surface of the porous hollow fiber membranes incorporated in the housing of the blood cleaning apparatus and to the inner surface of pores is carried out after the apparatuses have been assembled, it is advantageous in fact that the gamma ray irradiation also serves the purpose of sterilizing the blood cleaning apparatuses.

Further this invention is directed to a method which is characterized by using a plurality of blood cleaning apparatuses each constructed by arranging a multiplicity of porous hollow fiber membranes inside a housing, causing the empty spaces in the hollow fiber membranes to communicate with first fluid inlet and outlet provided in the housing thereby forming a first fluid passing space and causing the empty space defined by the inner surface of the housing and the outer surface of the porous hollow fiber membranes to communicate with second fluid inlet and fluid outlet thereby forming a second fluid passing space partitioned from the first fluid passing space, thereby enabling a plurality of steps of cleaning operation to be carried out continuously by serially connecting either the first fluid passing spaces or the second fluid passing spaces of the blood cleaning apparatuses thereby forming blood flow paths, arranging the connected blood flow paths substnatially linearly, passing the blood subjected to cleaning through the linearly arranged blood flow paths, and meanwhile feeding munutally different or similar cleaning liquids through the remaining plurality of second or first fluid passing spaces. This method, therefore, enables a freeze preserved blood cleaning operation comprising a plurality of treatments to be continuously and easily carried out in a germfree state within a closed system. It contributes immensely to the growth of the frozen storage system for blood.

This invention also is directed to a method for the cleaning of freeze preserve blood, which method is characterized by using a plurality of blood cleaning apparatuses each constructed by arranging a multiplicity of porous hollow fiber membranes inside a housing, causing the empty spaces in the hollow fiber membranes to communicate with first fluid inlet and outlet provided in the housing thereby forming a first fluid passing space and causing the empty space defined by the inner surface of the housing and the outer surface of the porous hollow fiber membranes to communicate with second liquid inlet and fluid outlet thereby forming a second fluid passing space partitioned from the first fluid passing space, thereby enabling a plurality of steps of cleaning operation to be carried out continuously by serially connecting either the first fluid passing spaces or the second fluid passing spaces of the blood cleaning apparatuses thereby forming blood flow paths, arranging the connected blood flow paths substantially linearly, causing some of either the first fluid passing spaces or the second fluid passing spaces of the plurality of blood cleaning apparatuses forming part of the blood flow path to be disposed in the direction of gravity and the remainders thereof to be disposed in a direction opposite the direction of gravity in the continued blood flow paths, passing the blood subjected to cleaning through the linearly arranged blood flow paths, and meanwhile feeding mutually different or similar cleaning liquids through the remaining plurality of second or first fluid passing spaces. This method, therefore, enables a freeze preserved blood cleaning operation comprising a plurality of treatments to be continuously and easily carried out in a germfree state within a closed system. It contributes immensely to the growth of the frozen storage system for blood.

What is claimed is:

1. A method of making a blood cleaning apparatus comprising: arranging inside a housing a multiplicity of blood cleaning hollow fiber membranes each comprising a hydrophobic porous hollow fiber membrane, causing the empty spaces inside said hollow fiber membranes to communicate with a blood inlet and a blood outlet disposed in said housing, causing the empty spaces defined by the inner surfaces of said housing and the outer surface of said porous hollow fiber membranes to communicate with a cleaning liquid inlet and a cleaning liquid outlet disposed in said housing, filling the inner empty space of the hydrophobic porous hollow fiber membranes with a hydrophilic compound, and concurrently sterilizing the apparatus and forming a hydrophilic thin layer at least on the inner surface of said hollow fiber membrane by the grafting of the hydrophilic compound through the agency of gamma rays.

2. A method according to claim 1, wherein said hydrophilic compound is glycerol.

3. A method according to claim 1, wherein said hydrophobic porous hollow fiber membrane is formed of one member selected from the group consisting of polyolefin type, polyester type, polyamide type, polyurethane type, poly(meth)acrylate type, poly(meth)acrylonitrile type, polysulfone type, and polyvinyl chloride type compounds and polymer blends thereof.

4. A method according to claim 3, wherein said hydrophobic porous hollow fiber membrane is made of polypropylene.

5. A method according to claim 1, wherein said blood cleaning hollow fiber membranes each possess an inside diameter in the range of 100 to 500 μm, and a wall thickness in the range of 5 to 30 μm.

6. A method according to claim 1, wherein said blood cleaning hollow fiber membranes each possess an average pore diameter in the range of 0.001 to 6.5 μm and a void ratio in the range of 30 to 70%.

* * * * *